United States Patent [19]
Godrich et al.

[11] 4,331,031
[45] May 25, 1982

[54] METHOD AND APPARATUS FOR TESTING THE RAIN RESISTANCE OF FABRICS AND GARMENTS OR OTHER ARTICLES MADE THEREFROM

[76] Inventors: Jonathan E. Godrich, Ludford Mill, Ludlow, Shropshire; David M. Towers, Rowden Mill, Rowden Bromyard, Herefordshire, both of England

[21] Appl. No.: 115,887

[22] Filed: Jan. 28, 1980

[30] Foreign Application Priority Data

Feb. 2, 1979 [GB] United Kingdom ............... 7903737

[51] Int. Cl.³ ............................................. G01N 33/36
[52] U.S. Cl. .................................................... 73/159
[58] Field of Search ...................... 73/38, 73, 159, 160

[56] References Cited
U.S. PATENT DOCUMENTS 2,012,762  8/1935  Kern ........................................ 73/159

FOREIGN PATENT DOCUMENTS 1445516  8/1976  United Kingdom .

Primary Examiner—S. Clement Swisher
Attorney, Agent, or Firm—Oblon, Fisher, Spivak, McClelland & Maier

[57] ABSTRACT

Rain resistance of fabrics and garments or other articles made therefrom is tested by subjecting the fabric or article to simulated rain and observing the time taken to first penetration, then observing the extent of penetration after a predetermined time after the first penetration. The longer the time to first penetration, and the less penetration after a given further time, the more resistant is the fabric. Penetration is determined by the penetrated rain altering the electrical resistance between contacts in an array; and the extent of penetration is observed by displaying the contacts made.

10 Claims, 2 Drawing Figures

METHOD AND APPARATUS FOR TESTING THE RAIN RESISTANCE OF FABRICS AND GARMENTS OR OTHER ARTICLES MADE THEREFROM

BACKGROUND OF THE INVENTION

1. Field of the Invention

This invention relates to methods and apparatus for testing the rain-resistance of fabrics and garments or other articles made therefrom.

2. Description of the Prior Art

One way of testing the rain-resistance of fabrics or garments that involves the simulation of natural rain characteristics is known. The time taken for the simulated rain to penetrate the fabric or garment is noted for example by causing the change in resistance between two electrical contacts at the back of the fabric to stop the test and a timing clock. Clearly, the longer the time to penetration, the better is the fabric or garment at resisting rain.

SUMMARY OF THE INVENTION

The present invention provides a modification to this kind of test that supplies more useful information about the fabric or garment.

The invention includes a method for testing the rain-resistance of fabrics and garments or other articles made therefrom in which the fabric or article is subjected to simulated rain and the time taken for the rain first to penetrate the sample is measured. The shower is continued for a predeterined time and the extent of penetration is measured.

The measurements may be made automatically, as by detecting a change of electrical resistance brought about at the back of the fabric by penetration.

The invention also includes apparatus for testing the rain resistance of fabrics and garments or other articles made therefrom in which the fabric or article is subjected to simulated rain, including a timing mechanism adapted to time the first penetration and a mechanism which can measure the extent of penetration at a preselected time after the first penetration.

The apparatus includes a penetration detector including an arrangement of electrical contacts over which the fabric or article can be placed and indicator mechanism to indicate a reduction in resistance due to penetrated rain. The indicator mechanism includes a display mechanism showing places on the fabric or article where penetration has occurred, and may, for example, include an array of light emitting diodes corresponding in layout to an array of regions on a contact panel on which the fabric is laid and connected so that wherever penetration occurs the corresponding diode lights up. In this way, the uniformity of fabric proofing treatment, or the effect of seams in a garment can be observed.

A timing mechanism is arranged to record the time of first penetration and a second presettable timer is started at that time and arranged to stop the test after the elapse of a further preselected period up to, say, 60 minutes.

BRIEF DESCRIPTION OF THE DRAWINGS

Various other objects, features and attendant advantages of the present invention will be more fully appreciated as the same becomes better understood from the following detailed description when considered in connection with the accompanying drawings in which like reference characters designate like or corresponding parts throughout the several views and wherein.

DETAILED DESCRIPTION OF THE PREFERRED EMBODIMENT

Figure 1:
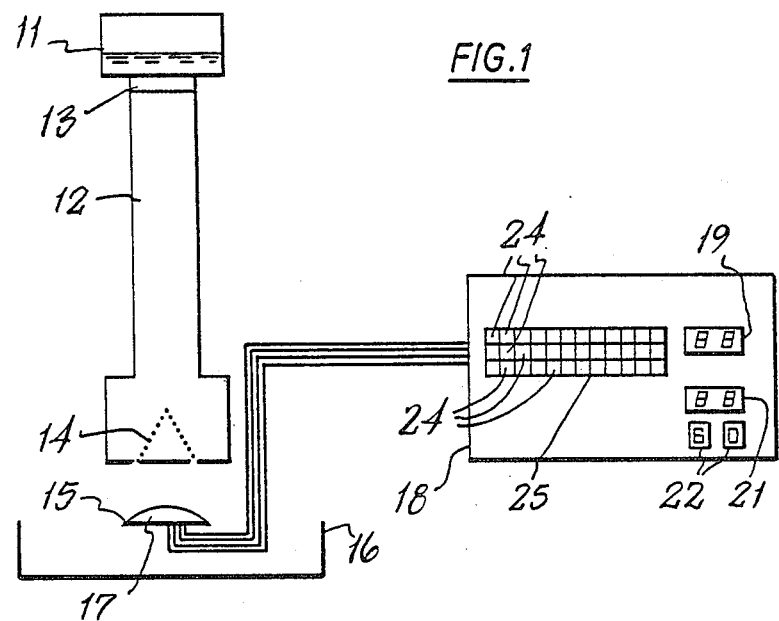
FIG. 1 is a schematic diagram of the apparatus.
Figure 2:
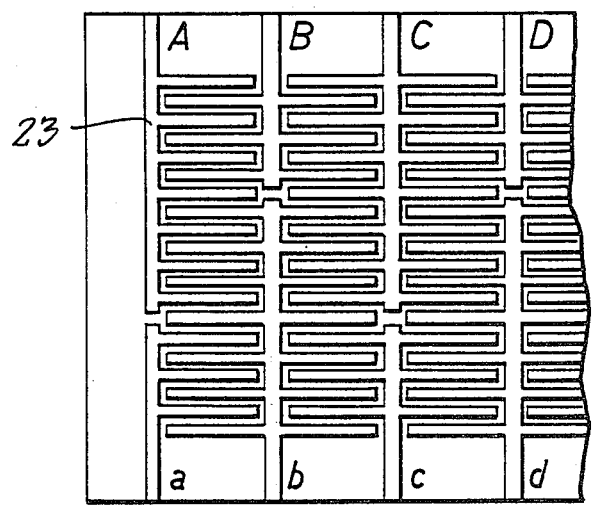
FIG. 2 is a view of part of a circuit board used as a detector in the apparatus.

FIG. 1 illustrates an arrangement, in which a constant head water reservoir 11 (preferably supplied with distilled water) sits on a column 12 down which water droplets, from a suitable drop producing arrangement 13 connected to the reservoir, fall on to a mesh drops splitter 14 in the shape of a cone. The splitter 14 converts the large droplets into smaller droplets which correspond in size and kinetic energy, when they fall on to a test sample 15, to a natural rain shower. A tray 16 beneath the sample 15 collects water that runs off, and water is circulated—so that large amounts of distilled water need not be used wastefully—all as previously known.

The present apparatus differs from such known apparatus in two respects, namely the nature of the pattern of conductive strips on the detector pad 17 on which the sample 15 is placed, and the control and display unit 18 to which the detector pad 17 is connected.

As before, the control and display unit 18 includes a timer 19 that is arranged to be started at the beginning of a test (i.e. when water droplets are first released from the arrangement 13) and stopped when water is first detected to have penetrated the sample, by virtue of it causing a short circuit on the pad 17. Unlike the previous arrangement, however, the detection of water penetration does not now bring the test to an end—rather the simulated shower is continued at this stage, and a second timer 21 is started. This timer 21 is presettable (by thumb wheel switches 22) to any number of minutes up to sixty. The test is eventually stopped when the preselected time has elapsed; that is to say, the circulation of water to the reservoir 11 is stopped, cutting off the shower, and a visible and/or audible warning signal is given.

The pad 17 is essentially a printed circuit board, on a flexible substrate so that it can be laid on a "mushroom head" support for the sample, for example, to simulate the natural curve of a shoulder. The conductive strips 23 are laid out in a pattern between edge connectors A, B, C, D etc. and a, b, c, d etc. on opposite edges of the pad 17. If there are twelve edge connectors on each edge, the pattern shown divides the pad 17 up into an array of thirty six sections, namely, those between connectors A and B, a and b, A and b, B and C, b and C, b and c and so on. The connectors A, B, C etc. a, b, c etc. are connected via a suitable logic arrangement to a 3×12 array 25 of light emitting diodes 24 so that the position of a short circuit on the pad 17 is indicated by the illumination of one of the diodes 24.

Preferably, to avoid the need to examine the display as soon as the test is finished, a latching mechanism is provided in the electronic circuit activating the diodes 24 so that when timer 21 signals the end of the test, those diodes already illuminated are so maintained, and the rest prevented from switching on. This avoids the information in the display becoming distorted or destroyed by wicking or by drying out, if the test is left unattended for any length of time after completion of the shower.

A meter can be provided connected to measure the total current across the detector pad 17 to give an indication of the degree of absorption—the wetter the fabric gets, the higher is the current flow.

Obviously, numerous modifications and variations of the present invention are possible in light of the above teachings. It is therefore to be understood that within the scope of the appended claims, the invention may be practiced otherwise than as specifically described herein.

What is claimed is:

1. A method for testing the rain-resistance of a fabric which comprises:

subjecting the front of the fabric to simulated rain;

detecting the first rain to penetrate through the fabric to the back of the fabric;

measuring the elapsed time for the rain to first penetrate through to the back of the fabric;

continuing the simulated rain on the front of the fabric for a predetermined time after the elapsed time;

detecting the total penetration of the rain through to the back of the fabric; and observing the total degree of the penetration of the rain to the back of the fabric at the end of the predetermined time.

2. The method according to claim 1 using a penetration detector comprising a plurality of electrical contacts arranged in a grid and positioned under the back of said fabric and wherein measuring the elapsed time further comprises detecting a first change in the electrical resistance on any one of the electrical contacts on the back of the fabric.

3. The method according to claim 2, wherein detecting of the total penetration of the rain further comprises detecting any change in electrical resistance at each electric contact of said plurality of electrical contacts on the back of the fabric.

4. The method according to claim 3 using a current meter connected to the penetration detector and wherein observing of the total degree of the penetration further comprises measuring the current in the current meter.

5. An apparatus for testing the rain resistance of a fabric in which the front of the fabric is subjected to simulated rain which penetrates through to the back of the fabric, comprising:

means for detecting the penetration of the rain through the fabric to the back of the fabric;

means for measuring the elapsed time for the rain to first penetrate through the back of the fabric;

means for preselecting a time after the first penetration through to the back of the fabric; and means for measuring the degree of the penetration to the back of the fabric at said preselected time after the first penetration.

6. The apparatus according to claim 5, wherein said detecting means further comprises:

a penetration detector comprising a plurality of electrical contacts arranged in a grid and positioned under the fabric; and indicator means for indicating a reduction in the electrical resistance of the electrical contacts due to the rain penetration to the back of the fabric above said contacts.

7. The apparatus according to claim 6 further comprising:

means for starting the means for preselecting a time after the time of first penetration; and wherein said indicator means further comprises display means for showing places on said fabric where penetration has be detected.

8. The apparatus according to claim 7, said display means further comprising an array of point indicators arranged in a grid similar to the grid of the electrical contacts.

9. The apparatus according to claim 5, wherein said detecting means further comprises a printed circuit board on a flexible substrate.

10. The apparatus according to claim 6, wherein said indicator means further comprises an array of light emitting diodes.

* * * * *